(12) United States Patent  
Miyahara et al.

(10) Patent No.: US 9,207,412 B2
(45) Date of Patent: Dec. 8, 2015

(54) OPTICAL TRANSMISSION MODULE AND ENDOSCOPE

(71) Applicant: OLYMPUS CORPORATION, Tokyo (JP)

(72) Inventors: Hideharu Miyahara, Nagano (JP); Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/498,067

(22) Filed: Sep. 26, 2014

(65) Prior Publication Data

US 2015/0086162 A1   Mar. 26, 2015

(30) Foreign Application Priority Data

Sep. 26, 2013 (JP) ................. 2013-199892
Jun. 19, 2014 (JP) ................. 2014-126599

(51) Int. Cl.
*G02B 6/32* (2006.01)
*G02B 6/42* (2006.01)
*G02B 23/24* (2006.01)

(52) U.S. Cl.
CPC ............... *G02B 6/4204* (2013.01); *G02B 6/32* (2013.01); *G02B 6/4274* (2013.01); *G02B 6/4296* (2013.01); *G02B 23/2423* (2013.01); *G02B 23/2446* (2013.01); *G02B 23/2469* (2013.01); *G02B 23/2484* (2013.01)

(58) Field of Classification Search
CPC ...... G02B 6/32; G02B 6/4206; G02B 6/4214; G02B 6/4204; G02B 6/4246
USPC ........................................ 385/15, 31, 33, 39
See application file for complete search history.

(56) References Cited

U.S. PATENT DOCUMENTS

| 4,784,144 A | * | 11/1988 | Ono et al. ............... 600/325 |
| 2003/0071318 A1 | * | 4/2003 | Wang ..................... 257/434 |
| 2004/0252951 A1 | * | 12/2004 | Nagasaka et al. ........... 385/88 |
| 2008/0285303 A1 | * | 11/2008 | Matsui et al. ............ 362/580 |
| 2011/0199781 A1 | * | 8/2011 | Okuno et al. ............ 362/555 |

FOREIGN PATENT DOCUMENTS

| EP | 0620460 A1 | * | 10/1994 |
| EP | 0887865 A1 | * | 12/1998 |
| JP | 2013-025092 A |   | 2/2013 |

* cited by examiner

*Primary Examiner* — Jennifer Doan
(74) *Attorney, Agent, or Firm* — Scully, Scott, Murphy & Presser, P.C.

(57) ABSTRACT

An optical transmission module includes: an optical device having a light emitting section that outputs light of an optical signal; an optical fiber that transmits the optical signal; a holding member in which a distal end portion of the optical fiber is inserted into a through hole having an inner diameter equivalent to an outer diameter of the optical fiber, and that is disposed on the optical device; and a lens section that is disposed in an opening on the optical device side of the through hole of the holding member, and that concentrates the light.

15 Claims, 7 Drawing Sheets

OPTICAL TRANSMISSION MODULE AND ENDOSCOPE

CROSS REFERENCE TO RELATED APPLICATIONS

This application claims the benefit of Japanese Patent Application No. 2013-199892 filed in Japan on Sep. 26, 2013 and Japanese Patent Application No. 2014-126599 filed in Japan on Jun. 19, 2014, the contents of which are incorporated in the specification, the claims, and the drawings of this application by this reference.

BACKGROUND OF THE INVENTION

1. Field of the Invention

The present invention relates to an optical transmission module including an optical device, an optical fiber, and a holding member in which the optical fiber is inserted, and an endoscope with the optical transmission module.

2. Description of the Related Art

In endoscopes, an image pickup section including an image pickup device, such as a CCD, is provided in a distal end portion of an elongated insertion section. In recent years, use of image pickup devices with a high pixel count in endoscopes has been studied. When an image pickup device with a high pixel count is used, a signal amount transmitted from the image pickup device to a signal processing apparatus increases. Thus, optical signal transmission via an optical fiber using optical signals is preferably employed instead of electrical signal transmission via a metal wire using electrical signals. In the optical signal transmission, an E/O module (electrical-optical converter) that converts electrical signals to optical signals, and an O/E module (optical-electrical converter) that converts optical signals to electrical signals are used.

For example, Japanese Patent Application Laid-Open Publication No. 2013-025092 discloses an optical transmission module including an optical device where an optical signal is inputted or outputted, a board on which the optical device is mounted, and a holding section that has a through hole into which an optical fiber is inserted for transmitting the optical signal inputted and outputted to and from the optical device, and is mounted and arranged to be aligned with the optical device in a thickness direction.

In the optical transmission module, it is necessary to perform accurate positioning of relative positions of the optical device and the holding section (ferrule) where the optical fiber is inserted. That is, when a center position of a light emitting section of the optical device and a center position of the through hole of the holding section are out of alignment, a light intensity or the like entering the optical fiber decreases, and the signal is attenuated.

Here, to reduce a burden on a subject and ensure an observation field of view, an outer diameter and a length of the distal end portion of the insertion section of the endoscope are preferably reduced as much as possible. Therefore, the optical transmission module for endoscopes is much smaller than an optical transmission module for normal communications. Consequently, particularly accurate positioning is required between the optical device and the optical fiber.

SUMMARY OF THE INVENTION

An optical transmission module according to an embodiment of the present invention includes: an optical device having a light emitting section that outputs light of an optical signal, or a light receiving section to which light of an optical signal is inputted; an optical fiber that transmits the optical signal; a holding member in which a distal end portion of the optical fiber is inserted into a through hole having an inner diameter equivalent to an outer diameter of the optical fiber, and that is disposed on the optical device; and a lens section that is disposed in an opening on the optical device side of the through hole of the holding member, and that concentrates or diffuses the light.

An endoscope according to another embodiment includes, in a distal end portion of an insertion section, an optical transmission module including: an optical device having a light emitting section that outputs light of an optical signal, or a light receiving section to which light of an optical signal is inputted; an optical fiber that transmits the optical signal; a holding member in which a distal end portion of the optical fiber is inserted into a through hole having an inner diameter equivalent to an outer diameter of the optical fiber, and that is disposed on the optical device; and a lens section that is disposed in an opening on the optical device side of the through hole of the holding member, and that concentrates or diffuses the light.

DETAILED DESCRIPTION OF THE PREFERRED EMBODIMENTS

First Embodiment

An optical transmission module 1 according to a first embodiment is described by using FIGS. 1 to 5. The optical transmission module of the present embodiment is an E/O module that converts an electrical signal to an optical signal and transmits the optical signal.

The optical transmission module 1 includes an optical device 10, a wiring board 20, a lens section 30, a holding member 40, and an optical fiber 50. In the optical transmission module 1, the optical device 10, the wiring board 20, and the holding member 40 are arranged sequentially in a thickness direction (a Z direction) of the optical device 10.

For example, the optical device 10 is a surface emitting laser having a light emitting section 11 that outputs light of an optical signal. The ultra-small optical device 10 having a size in plan view of, for example, 250 μm×300 μm includes the light emitting section 11 having a diameter of 12 μm, and an electrode 12 that supplies a drive signal to the light emitting section 11.

The optical fiber 50 transmits the optical signal. In the holding member 40 disposed on the optical device 10, the optical fiber 50 is inserted into a through hole 40H having an inner diameter substantially equivalent to an outer diameter of the optical fiber 50. The lens section 30 that concentrates the light is disposed in an opening on the optical device side (a lower side) of the through hole 40H of the holding member 40.

The optical device 10 is flip-chip-mounted on the wiring board 20. That is, the wiring board 20 has a wire (not shown) connected to the electrode 12 of the optical device 10. An FPC board, a ceramic board, a glass epoxy board, a glass board, a silicon board or the like are used as a substrate of the wiring board 20. For example, an Au bump of the optical device 10 and a connection electrode section (not shown) of the wiring board 20 are ultrasonically bonded. Although not shown in the drawings, an adhesive, such as an underfill material and a sidefill material, is injected into a bonded portion. The optical device 10 may be also mounted on the wiring board 20 by printing a solder paste or the like on the wiring board 20, and melting the solder by reflowing or the like after arranging the optical device 10. The wiring board 20 may include a processing circuit, for example, for converting an electrical signal from an image pickup section to a drive signal of the optical device 10.

The through hole 40H having a columnar shape, the inner diameter of which is substantially equivalent to the outer diameter of the optical fiber 50 to be inserted into the through hole 40H, is formed in the holding member 40 having a substantially rectangular parallelepiped shape. In addition to the columnar shape, the through hole 40H may also have a prismatic shape as long as the optical fiber 50 can be held by an inner face of the through hole 40H. For example, a material of the holding member 40 is ceramic, Si, glass, or a metal member such as SUS. Note that the holding member 40 may have a substantially columnar shape or a substantially conical shape as well as the substantially rectangular parallelepiped shape.

In the optical transmission module 1 of the embodiment, a lower portion of the through hole 40H has an increasing sectional area toward an opening face 41S1 on the optical device side. The lens section 30 is fitted and adhered to the portion. That is, an inner face shape of the lower portion of the through hole 40H is substantially equivalent to an outer face shape of the lens section 30. Note that a recess portion larger than the outer face shape of the lens section 30 may be partially formed in the inner face shape of the lower portion of the through hole 40/H as long as the lens section 30 can be fitted. When the recess portion is formed in the through hole 40H, an adhesive used for adhesion does not protrude outside even when an excess amount of adhesive is applied. Accordingly, the lens section 30 can be reliably adhered.

Figure 1:
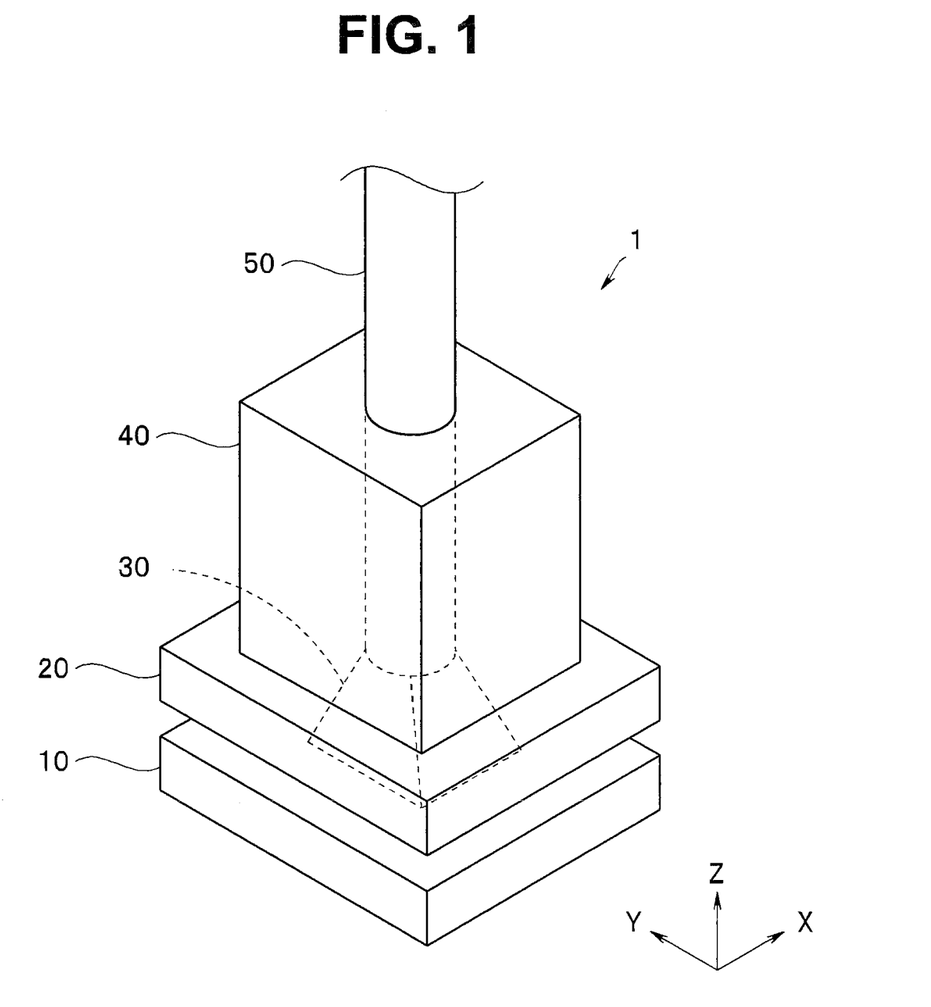
FIG. 1 is a perspective view of an optical transmission module according to a first embodiment.
Figure 2:
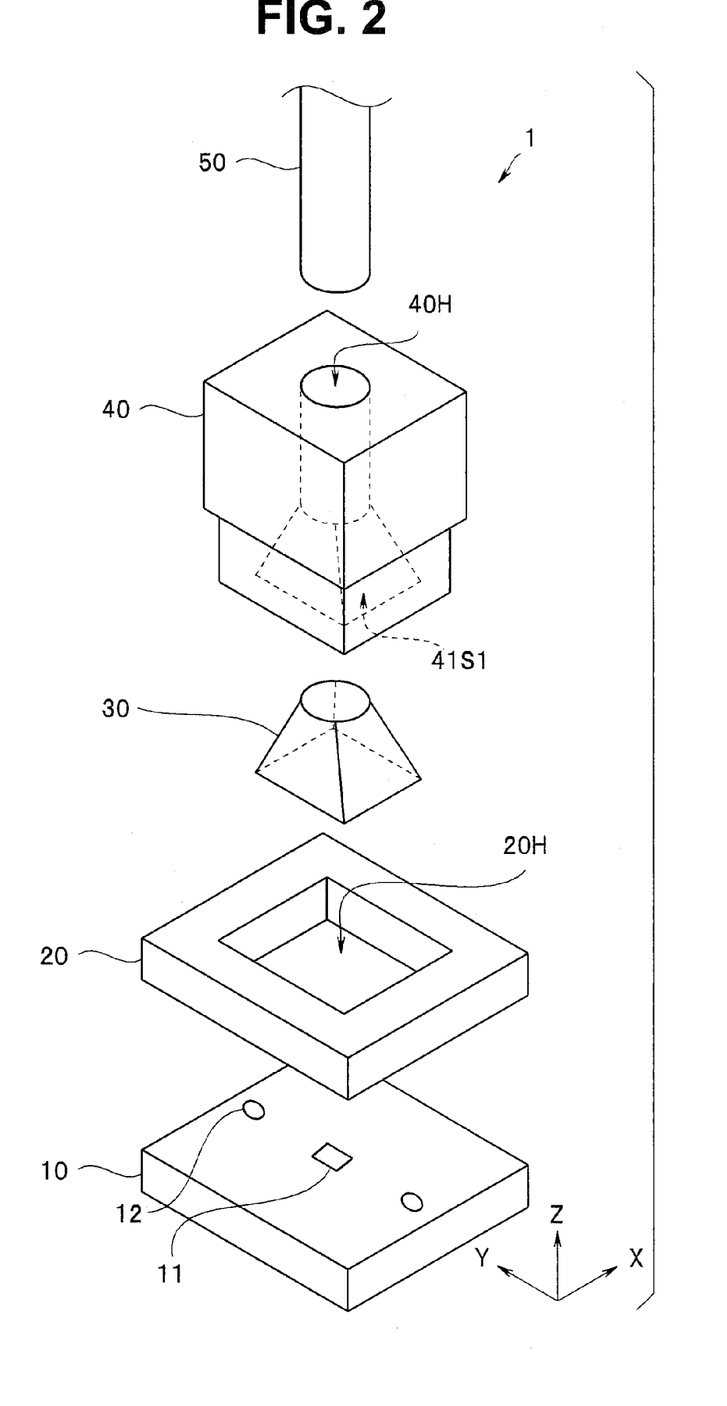
FIG. 2 is an exploded view of the optical transmission module according to the first embodiment.
Figure 3:
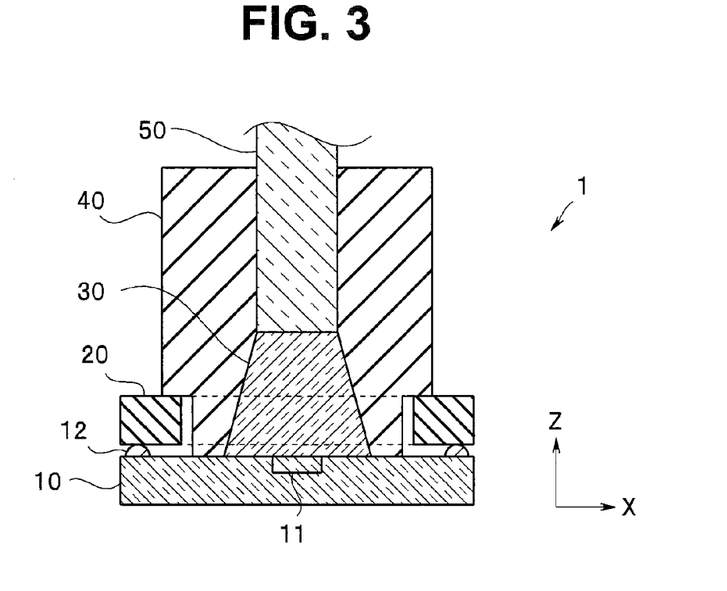
FIG. 3 is a sectional view of the optical transmission module according to the first embodiment.

The lens section 30 has a quadrangular bottom face, and a circular upper face, and has an increasing sectional area from the upper face toward the lower face as shown in FIG. 2.

The lens section 30 that concentrates the light is made of a transparent material having a high refractive index, e.g., glass or resin.

One distal end portion of the optical fiber 50 is inserted into the through hole 40H of the holding member 40. For example, the optical fiber 50 having a diameter of 125 μm is composed of a light-transmitting core having a diameter of 50 μm, and a clad covering an outer periphery of the core.

Here, an effect of the lens section is described based on an example in which light with a radiation angle of 25° radiated from the light emitting section 11 having a diameter of 12 μm is caused to enter the core having a diameter of 50 μm.

If a distance between the light emitting section 11 and a distal end face of the optical fiber 50 is 85 μm or more, a portion of the light radiated from the light emitting section 11 does not enter the core of the optical fiber 50. On the other hand, in a case in which the lens section made of glass having a refractive index of 1.55 is disposed, all the light from the optical device 10 enters the core of the optical fiber 50 when an angle of inclination (slant face) of the lens section 30 is about 52° or more. By disposing the lens section, the distance between the light emitting section 11 and the distal end face of the optical fiber 50 can be also decreased.

When the optical transmission module 1 is manufactured, for example, the optical device 10 is mounted on the wiring board 20, and the lens section 30 is adhered immediately on the light emitting section 11 of the optical device 10 by a transparent adhesive (not shown). By using the lens section 30 as a positioning member, the holding member 40 is adhered by a transparent adhesive (not shown) in a state fitted with the lens section 30. The optical fiber 50 is inserted into the through hole 40H of the holding member 40. Since there is a slight gap between a wall face of the through hole 40H and a side face of the optical fiber 50, the distal end portion of the optical fiber 50 is fixed to the through hole 40H of the holding member 40 with the transparent adhesive filling the gap.

Figure 4:
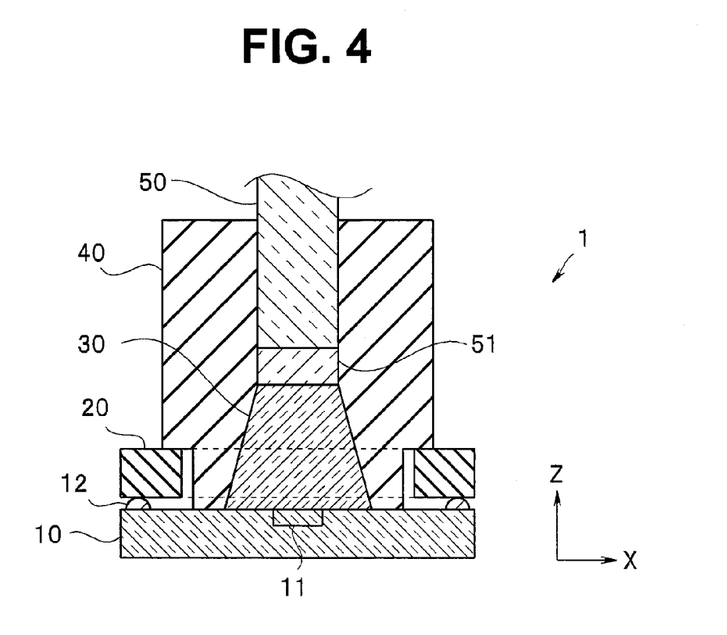
FIG. 4 is a sectional view of the optical transmission module according to the first embodiment.
Figure 5:
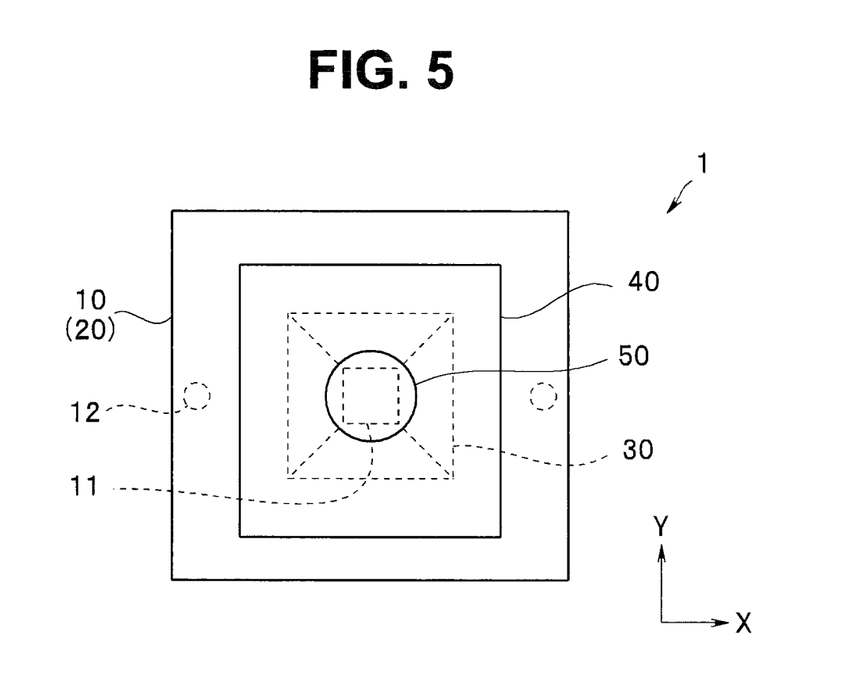
FIG. 5 is a top view of the optical transmission module according to the first embodiment.

As shown in FIG. 4, a transparent resin 51 having a given thickness or more (e.g., 2 to 20 μm) may be also filled between the end face of the optical fiber 50 and the lens section 30. The transparent resin 51 is composed of an optical adhesive having a transmittance of, for example, 90% or more. The transparent resin 51 preferably has a refractive index substantially equivalent to that of the lens section 30, and more specifically, may have a refractive index of 1.4 to 1.6. Since the transparent resin 51 is filled between the optical fiber 50 and the lens section 30, an airspace does not exist between the optical fiber 50 and the lens section 30. Therefore, attenuation by reflection at an interface between the lens section 30 and the airspace can be reduced. Moreover, the optical fiber 50 can be more rigidly fixed to the lens section 30 and the holding member 40.

Figure 6:
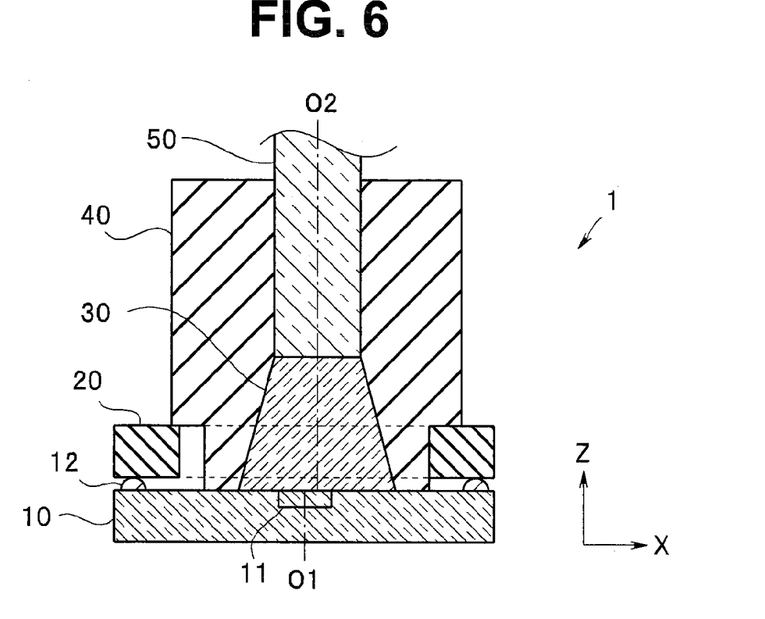
FIG. 6 is a sectional view of the optical transmission module according to the first embodiment.

As shown in FIG. 6, in the optical transmission module 1, even when a center O1 of the light emitting section 11 of the optical device 10 and a center of the lens section 30, i.e., a center O2 of the optical fiber 50 are arranged slightly out of alignment, the light generated by the light emitting section 11 is concentrated on a center portion of the lens section 30, and guided into the core of the optical fiber 50.

Since it is not necessary to increase positioning accuracy of the optical device 10 and the optical fiber 50, the optical transmission module 1 has high productivity.

Moreover, in the optical transmission module 1, the lens section 30 is fitted to the lower portion of the through hole 40H having the inner face shape equivalent to the outer face shape of the lens section 30. Thus, the lens section 30 and the holding member 40 are uniquely positioned. Therefore, the productivity is high.

Note that the upper face of the lens section 30 only needs to have a size equivalent to or smaller than the diameter of the optical fiber 50, and more preferably, equivalent to or smaller than the core diameter of the optical fiber 50. While the light concentration effect is obtained when the lower face has a larger area than that of the upper face, it is preferable that the lower face area is twice or more to 20 times or less of the upper face area. When the area is within the above range, good productivity is obtained. When the area is equivalent to or smaller than the above range, an outer diameter of the optical transmission module 1 falls within an allowable range so as to be used for endoscopes.

Modification

Since the lens section 30 shown in FIG. 2 has a substantially quadrangular pyramid shape with a flat upper face, a side face is a flat face. In other words, the wall face in the lower portion of the through hole 40H of the holding member 40 is a flat face.

Figure 7:
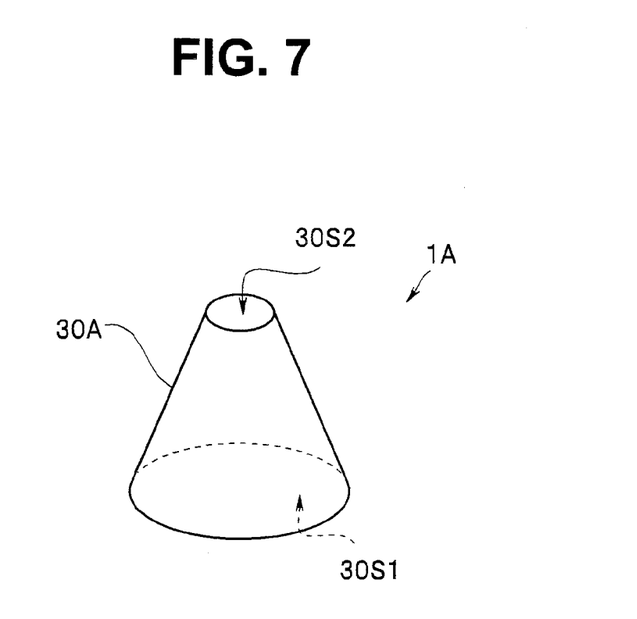
FIG. 7 is a perspective view of a lens section according to a modification of the optical transmission module of the first embodiment.

On the other hand, a lens section 30A of an optical transmission module 1A according to a modification of the first embodiment shown in FIG. 7 has a substantially conical shape with a flat upper face 30S2 and a flat lower face 30S1. Thus, a side face is a curved face. Therefore, the wall face in the lower portion of the through hole of the holding member, which is fitted with the lens section 30A, is a curved face.

Note that the shape of the lens section, i.e., the lower portion shape of the through hole of the holding member 40 is not limited to the substantially quadrangular pyramid shape or the substantially conical shape as in the lens sections 30 and 30A, and as long as the lower face has a larger area than the upper face, any shape may be employed.

Second Embodiment

Figure 8:
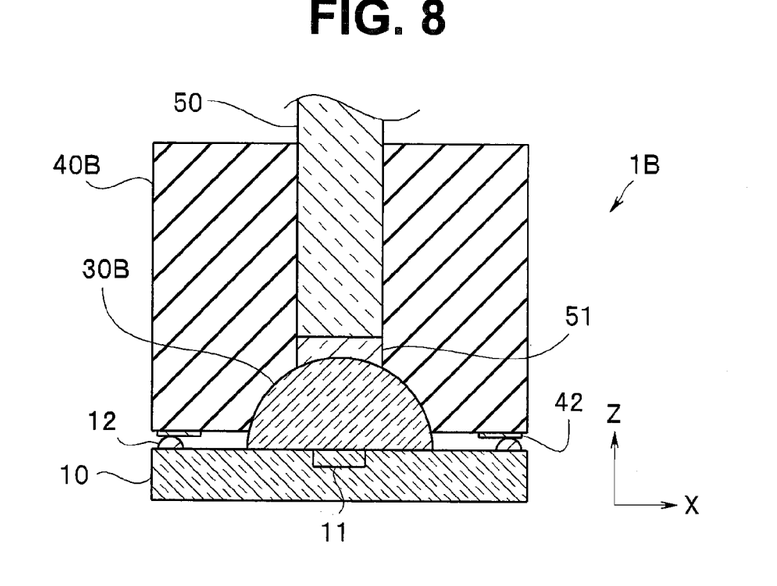
FIG. 8 is a sectional view of an optical transmission module according to a second embodiment.

Since an optical transmission module 1B according to a second embodiment is similar to the optical transmission module 1, constituent elements having the same functions are assigned the same reference numerals, and description thereof is omitted.

As shown in FIG. 8, the optical transmission module 1B has a wire 42 electrically connected to the optical device 10, on a lower face of a holding member 40B, and does not include the wiring board 20. That is, the holding member 40B is an MID (molded interconnect device) in which the wire 42 or the like connected to the electrode 12 of the optical device 10 is disposed on the lower face (a face opposing the optical device 10).

A lens section 30B has a hemispherical shape, and the inner face shape of the lower portion of the through hole, to which the lens section 30B is fitted, is a hemispherical shape. The transparent resin 51 is filled between the optical fiber 50 and the lens section 30B.

The optical transmission module 1B provides the effect of the optical transmission module 1. Moreover, since the wiring board is not required, the optical transmission module 1B has a small length.

Third Embodiment

Figure 9:
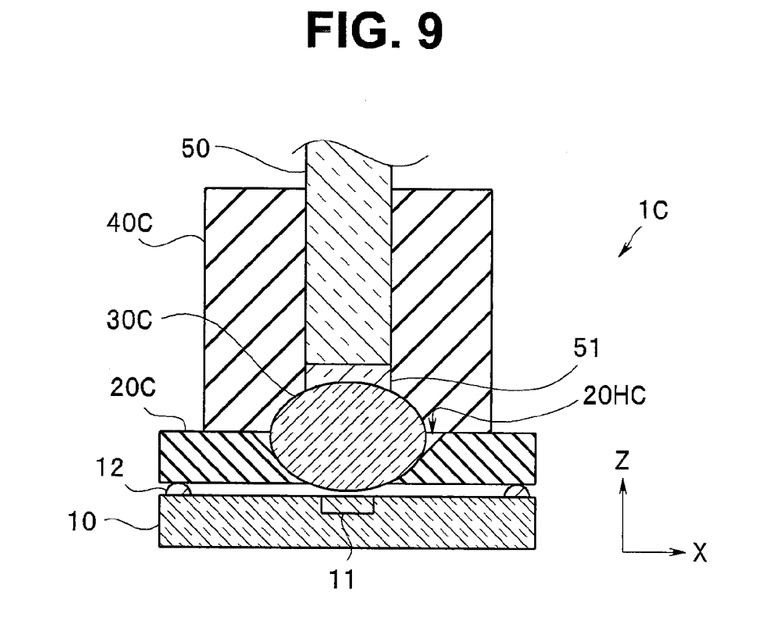
FIG. 9 is a sectional view of an optical transmission module according to a third embodiment.

Since an optical transmission module 1C according to a third embodiment is similar to the optical transmission module 1, constituent elements having the same functions are assigned the same reference numerals, and description thereof is omitted.

As shown in FIG. 9, in a wiring board 20C of the optical transmission module 1C, a wall face of a center through hole 20HC has a tapered shape so as to uniquely position a lens section 30C having a spheroidal shape to be disposed in the through hole 20HC. That is, an opening in an upper face of the through hole 20HC is larger than an opening in a lower face. The lower portion of the through hole of a holding member 40C has a shape equivalent to the shape of an upper portion of the lens section 30C, and the lens section 30C is fitted to the through hole.

The optical transmission module 1C provides the effect of the optical transmission module 1. Moreover, since the lens section 30C can be easily disposed at a predetermined position of the wiring board 20C, higher productivity is achieved.

Fourth Embodiment

Figure 10:
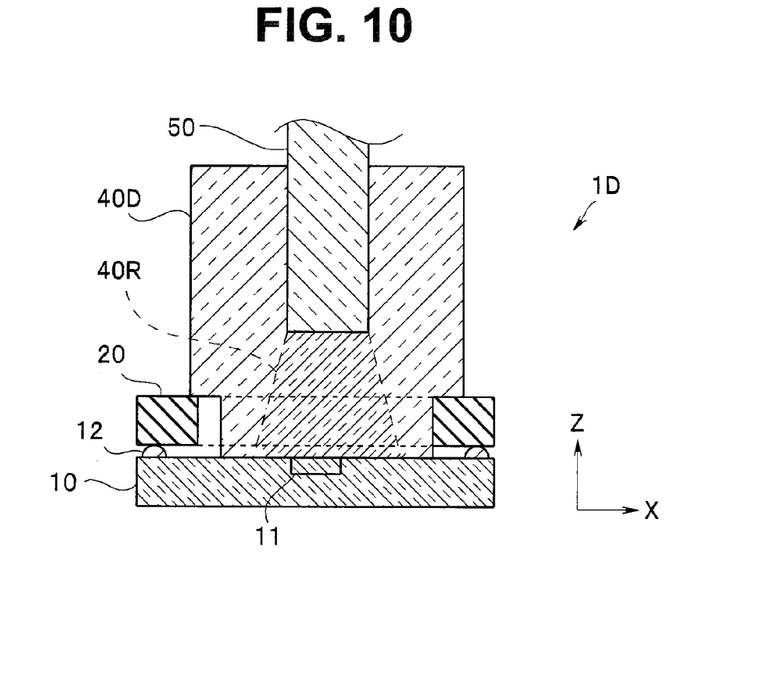
FIG. 10 is a sectional view of an optical transmission module according to a fourth embodiment.

Since an optical transmission module 1D according to a fourth embodiment is similar to the optical transmission module 1, constituent elements having the same functions are assigned the same reference numerals, and description thereof is omitted.

As shown in FIG. 10, in the optical transmission module 1D, a lens section 40R in the lower portion of the through hole of a holding member 40D is integrated with the holding member 40D. That is, the holding member 40D is also made of a transparent material, and the lens section 40R is made of a material having a higher refractive index than that of the holding member 40D.

Note that the holding member 40D only needs to be partially made of a transparent material. That is, at least the lens section 40R and a portion around the lens section 40R of the holding member 40D may be made of a transparent material.

The optical transmission module 1D provides the effect of the optical transmission module 1. Moreover, the optical transmission module 1D is easily assembled.

Note that the optical transmission module in the embodiments or the like described above is the E/O module including the surface emitting laser as the optical device. However, an O/E module in which a light receiving section composed of, for example, a photodiode (PD), to which light of an optical signal is inputted, is formed as the optical device, also provides the similar effect.

That is, an O/E module including an optical device that has a light receiving section, to which light of an optical signal is inputted, an optical fiber that transmits the optical signal, a holding member in which a distal end portion of the optical fiber is inserted into a through hole having an inner diameter equivalent to an outer diameter of the optical fiber, and that is disposed on the optical device, and a lens section that is disposed in an opening on the optical device side of the through hole of the holding member, and that diffuses the light provides the same effect as the E/O module of the embodiments or the like.

Fifth Embodiment

Figure 11:
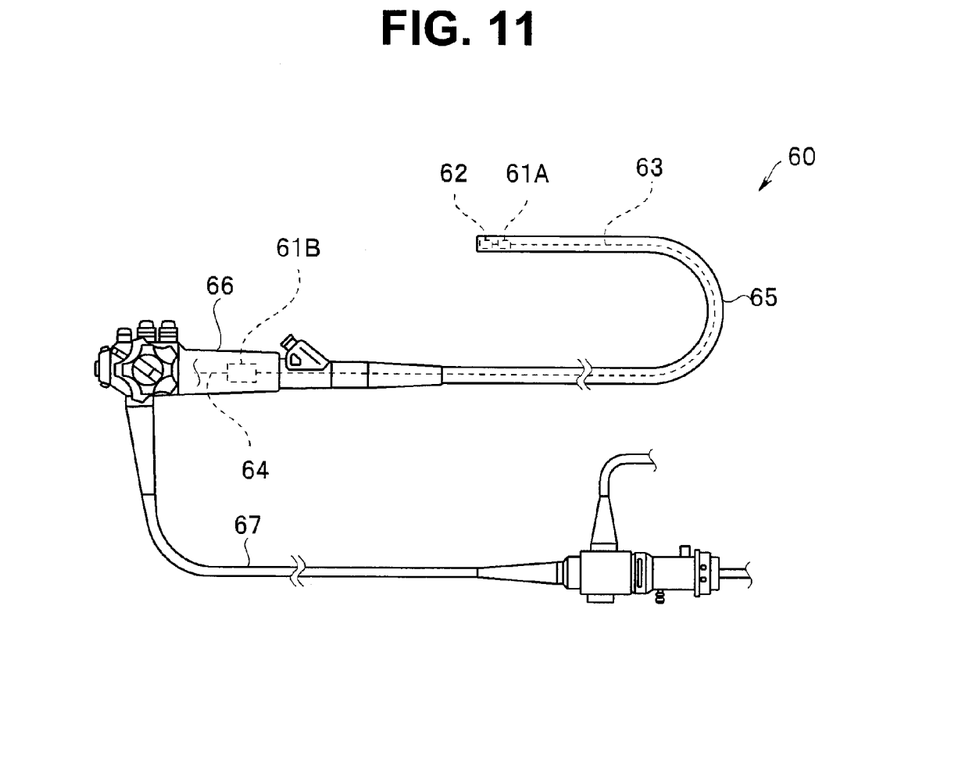
FIG. 11 is a perspective view of an endoscope according to a fifth embodiment.

Next, an endoscope 60 according to a fifth embodiment is described. Since optical transmission modules 61A and 61B of the endoscope 60 are the same as the optical transmission module 1 or the like of the embodiments of the present invention described above, description thereof is omitted.

As shown in FIG. 11, the endoscope 60 includes an insertion section 65 in which an image pickup section having an image pickup device with a high pixel count is disposed in a distal end portion 62, an operation section 66 that is disposed on a proximal end side of the insertion section 65, and an universal cord 67 that extends from the operation section 66.

An electrical signal outputted from the image pickup section is converted to an optical signal by the E/O module 61A in which the optical device is a surface emitting laser. The optical signal passes through an optical fiber 63 to be converted again to an electrical signal by the O/E module 61B disposed in the operation section 66 and in which the optical device is a PD. The electrical signal is transmitted via a metal wire 64. That is, the signal is transmitted via the optical fiber 50 within the insertion section 65 having a small diameter.

Since the E/O module 61A has the same configuration as the optical transmission modules 1 to 1D or the like, the E/O module 61A is ultra-small, but has high productivity. Therefore, while the distal end portion and the insertion section of the endoscope 60 have a small diameter, the productivity is high.

Note that the O/E module 61B preferably has the same configuration as the E/O module 61A, i.e., the optical transmission modules 1 to 1D or the like of the present invention although an arrangement space for the O/E module 61B is relatively wide.

The invention described in the foregoing embodiments is not limited to the embodiments and modifications described above, and various modifications can be implemented within a range that does not deviate from the spirit and scope of the present invention in the implementing stage. Further, the above described embodiments include inventions of various stages, and various inventions can be extracted by appropriately combining a plurality of the disclosed configuration requirements.

What is claimed is:

1. An optical transmission module, comprising:
   an optical device having a light emitting section that outputs light of an optical signal, or a light receiving section to which light of an optical signal is inputted;
   a holding member in which a distal end portion of an optical fiber is inserted into a through hole having an inner diameter equivalent to an outer diameter of the optical fiber, and that is disposed on the optical device; and
   a lens section that is disposed in an opening on the optical device side of the through hole of the holding member, wherein the lens section is adhered to the optical device.

2. The optical transmission module according to claim 1, wherein the lens section is fitted to a lower portion of the through hole having an inner face shape equivalent to an outer face shape of the lens section.

3. The optical transmission module according to claim 2, wherein the lower portion of the through hole has an increasing sectional area toward the opening.

4. The optical transmission module according to claim 3, wherein a wall face of the lower portion of the through hole is a flat face.

5. The optical transmission module according to claim 3, wherein a wall face of the lower portion of the through hole is a curved face.

6. The optical transmission module according to claim 1, wherein a transparent resin is filled between the distal end portion of the optical fiber inserted into the through hole and the lens section.

7. The optical transmission module according to claim 1, wherein the optical device is a surface emitting laser provided with the light emitting section.

8. An endoscope comprising the optical transmission module according to claim 1 in a distal end portion of an insertion section.

9. The optical transmission module according to claim 1, wherein the lens section is adhered with a transparent adhesive to the optical device.

10. The optical transmission module according to claim 1, wherein the lens section is in contact with or is adhered to the light emitting section.

11. The optical transmission module according to claim 1, wherein a cross section of the lens section is a substantially rectangular parallelepiped shape.

12. The optical transmission module according to claim 1, wherein a cross sectional area of the lens section on the optical device side of the lens section is larger than a cross sectional area of the lens section on the side of the lens section that opposes the optical device side.

13. The optical transmission module according to claim 12, wherein the cross sectional area of the lens section on the optical device side of the lens section is two or more times larger than the cross sectional area of the lens section on the side of the lens section that opposes the optical device side.

14. The optical transmission module according to claim 1, wherein the holding member is in contact with or is adhered to the optical device.

15. The optical transmission module according to claim 1, wherein the holding member is in contact with or is adhered to the optical device and the holding member is in contact with or is adhered to the lens section.

* * * * *